United States Patent
Tsunemichi

(10) Patent No.: US 12,226,211 B2
(45) Date of Patent: Feb. 18, 2025

(54) ATTENTIVENESS DETERMINATION DEVICE, ATTENTIVENESS DETERMINATION SYSTEM, ATTENTIVENESS DETERMINATION METHOD, AND COMPUTER-READABLE STORAGE MEDIUM

(71) Applicant: Mitsubishi Electric Corporation, Tokyo (JP)

(72) Inventor: Daichi Tsunemichi, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 864 days.

(21) Appl. No.: 17/421,736

(22) PCT Filed: Jan. 21, 2019

(86) PCT No.: PCT/JP2019/001586
§ 371 (c)(1),
(2) Date: Jul. 9, 2021

(87) PCT Pub. No.: WO2020/152732
PCT Pub. Date: Jul. 30, 2020

(65) Prior Publication Data
US 2022/0095972 A1 Mar. 31, 2022

(51) Int. Cl.
*A61B 5/16* (2006.01)
*A61B 3/08* (2006.01)
(Continued)

(52) U.S. Cl.
CPC .............. *A61B 5/163* (2017.08); *A61B 3/085* (2013.01); *A61B 3/111* (2013.01); *A61B 3/113* (2013.01);
(Continued)

(58) Field of Classification Search
CPC ......... A61B 5/163; A61B 5/085; A61B 5/111; A61B 5/113; A61B 5/168
See application file for complete search history.

(56) References Cited

U.S. PATENT DOCUMENTS

2017/0156585 A1* 6/2017 Nie .................. A61B 3/085
2017/0169726 A1* 6/2017 Aguirre .............. G09B 5/02
(Continued)

FOREIGN PATENT DOCUMENTS

JP  11-276461 A  10/1999
JP  2013-233216 A  11/2013

OTHER PUBLICATIONS

International Search Report and Written Opinion mailed on Apr. 9, 2019, received for PCT Application PCT/JP2019/001586, Filed on Jan. 21, 2019, 7 pages including English Translation.

*Primary Examiner* — Benjamin O Dulaney
(74) *Attorney, Agent, or Firm* — XSENSUS LLP

(57) ABSTRACT

An attentiveness determination device includes an image processing unit, a pupil distance calculation unit, a heterophoria detection unit, and an attentiveness determination unit. The image processing unit outputs first reference coordinates, second reference coordinates, first pupil coordinates, and second pupil coordinates. The pupil distance calculation unit calculates at least one position component of the first pupil coordinates with respect to the first reference coordinates and at least one position component of the second pupil coordinates with respect to the second reference coordinates. The heterophoria detection unit outputs a heterophoria detection result indicating a state of a first eyeball and a second eyeball. The attentiveness determination unit determines attentiveness of a person according to the heterophoria detection result.

14 Claims, 8 Drawing Sheets

(51) Int. Cl.
*A61B 3/11* (2006.01)
*A61B 3/113* (2006.01)
*A61B 3/14* (2006.01)
*G06T 7/70* (2017.01)
*G06V 40/16* (2022.01)
*G06V 40/18* (2022.01)

(52) U.S. Cl.
CPC ................ *A61B 3/14* (2013.01); *A61B 5/168* (2013.01); *G06T 7/70* (2017.01); *G06V 40/161* (2022.01); *G06V 40/18* (2022.01); *G06T 2207/30041* (2013.01)

(56) References Cited

U.S. PATENT DOCUMENTS

| | | | | |
|---|---|---|---|---|
| 2018/0319407 | A1* | 11/2018 | Lisseman | G06V 20/597 |
| 2019/0367050 | A1* | 12/2019 | Victor | G06V 20/597 |
| 2021/0112226 | A1* | 4/2021 | Abou Shousha | A61B 3/14 |

\* cited by examiner

ATTENTIVENESS DETERMINATION DEVICE, ATTENTIVENESS DETERMINATION SYSTEM, ATTENTIVENESS DETERMINATION METHOD, AND COMPUTER-READABLE STORAGE MEDIUM

CROSS-REFERENCE TO RELATED APPLICATION

The present application is based on PCT filing PCT/JP2019/001586, filed Jan. 21, 2019, the entire contents of which are incorporated herein by reference.

TECHNICAL FIELD

The present invention relates to an attentiveness determination device, an attentiveness determination system, an attentiveness determination method, and a computer-readable storage medium.

BACKGROUND ART

There has been proposed an information presentation device that detects a saccadic eye movement based on face images of a person and determines an attentiveness level (also referred to simply as "attentiveness") of the person based on the occurrence frequency of the detected saccadic eye movement (see Patent Reference 1, for example).

PRIOR ART REFERENCE

Patent Reference

Patent Reference 1: Japanese Patent Application Publication No. 11-276461

SUMMARY OF THE INVENTION

Problem to be Solved by the Invention

The information presentation device described in the Patent Reference 1 detects a saccade that is a high-speed eye movement and determines the attentiveness level of an operator based on the occurrence frequency of the detected saccade. However, in order to capture images of a high-speed eye movement like the saccade, a camera capable of capturing images at a high frame rate is necessary. As a result, the cost for the information presentation device increases.

An object of the present invention, which is made to resolve the above-described problem, is to determine the attentiveness of a person by using images captured at a low frame rate.

MEANS FOR SOLVING THE PROBLEM

An attentiveness determination device according to an aspect of the present invention is an attentiveness determination device to use a captured image including a first eyeball and a second eyeball of a person, including:
a processor to execute a program; and
a memory to store the program which, when executed by the processor, performs processes of,
setting first reference coordinates regarding the first eyeball and second reference coordinates regarding the second eyeball in the captured image, calculating first pupil coordinates that are coordinates of a pupil of the first eyeball in the captured image and second pupil coordinates that are coordinates of a pupil of the second eyeball in the captured image, and outputting the first reference coordinates, the second reference coordinates, the first pupil coordinates, and the second pupil coordinates;
calculating at least one position component of the first pupil coordinates with respect to the first reference coordinates and at least one position component of the second pupil coordinates with respect to the second reference coordinates;
outputting a heterophoria detection result indicating a state of the first eyeball and the second eyeball by using the at least one position component of the first pupil coordinates and the at least one position component of the second pupil coordinates; and
determining attentiveness of the person according to the heterophoria detection result.

An attentiveness determination device according to another aspect of the present invention is an attentiveness determination device to use a captured image including a first eyeball and a second eyeball of a person, including:
a processor to execute a program; and
a memory to store the program which, when executed by the processor, performs processes of,
setting first reference coordinates regarding the first eyeball and second reference coordinates regarding the second eyeball in the captured image, calculating first pupil coordinates that are coordinates of a pupil of the first eyeball in the captured image and second pupil coordinates that are coordinates of a pupil of the second eyeball in the captured image, and outputting the first reference coordinates, the second reference coordinates, the first pupil coordinates and the second pupil coordinates;
calculating at least one position component of the first pupil coordinates with respect to the first reference coordinates and at least one position component of the second pupil coordinates with respect to the second reference coordinates;
normalizing the at least one position component of the first pupil coordinates and the at least one position component of the second pupil coordinates and outputting the normalized values as pupil distance correction values;
outputting a heterophoria detection result indicating a state of the first eyeball and the second eyeball by using the pupil distance correction values; and
determining attentiveness of the person according to the heterophoria detection result.

An attentiveness determination system according to another aspect of the present invention includes the attentiveness determination device described above.

An attentiveness determination method according to another aspect of the present invention is an attentiveness determination method of determining attentiveness of a person by using a captured image including a first eyeball and a second eyeball of the person, including:
setting first reference coordinates regarding the first eyeball and second reference coordinates regarding the second eyeball in the captured image;
calculating first pupil coordinates that are coordinates of a pupil of the first eyeball in the captured image and second pupil coordinates that are coordinates of a pupil of the second eyeball in the captured image;
outputting the first reference coordinates, the second reference coordinates, the first pupil coordinates and the second pupil coordinates;

calculating at least one position component of the first pupil coordinates with respect to the first reference coordinates and at least one position component of the second pupil coordinates with respect to the second reference coordinates;

outputting a heterophoria detection result indicating a state of the first eyeball and the second eyeball by using the at least one position component of the first pupil coordinates and the at least one position component of the second pupil coordinates; and determining the attentiveness of the person according to the heterophoria detection result.

An attentiveness determination method according to another aspect of the present invention is an attentiveness determination method of determining attentiveness of a person by using a captured image including a first eyeball and a second eyeball of the person, including:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates and the second pupil coordinates;

calculating at least one position component of the first pupil coordinates with respect to the first reference coordinates and at least one position component of the second pupil coordinates with respect to the second reference coordinates;

normalizing the at least one position component of the first pupil coordinates and the at least one position component of the second pupil coordinates;

outputting the normalized values as pupil distance correction values;

outputting a heterophoria detection result indicating a state of the first eyeball and the second eyeball by using the pupil distance correction values; and determining the attentiveness of the person according to the heterophoria detection result.

A computer-readable storage medium storing a program according to another aspect of the present invention is a computer-readable storage medium storing a program that causes a computer to execute an attentiveness determination method of determining attentiveness of a person by using a captured image including a first eyeball and a second eyeball of the person, the program causing the computer to execute:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates and the second pupil coordinates;

calculating at least one position component of the first pupil coordinates with respect to the first reference coordinates and at least one position component of the second pupil coordinates with respect to the second reference coordinates; and determining the attentiveness of the person according to the heterophoria detection result.

A computer-readable storage medium storing a program according to another aspect of the present invention is a computer-readable storage medium storing a program that causes a computer to execute an attentiveness determination method of determining attentiveness of a person by using a captured image including a first eyeball and a second eyeball of the person, the program causing the computer to execute:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates and the second pupil coordinates;

calculating at least one position component of the first pupil coordinates with respect to the first reference coordinates and at least one position component of the second pupil coordinates with respect to the second reference coordinates;

normalizing the at least one position component of the first pupil coordinates and the at least one position component of the second pupil coordinates;

outputting the normalized values as pupil distance correction values;

outputting a heterophoria detection result indicating a state of the first eyeball and the second eyeball by using the pupil distance correction values; and determining the attentiveness of the person according to the heterophoria detection result.

Effect of the Invention

According to the present invention, the attentiveness of a person can be determined by using images captured at a low frame rate.

MODE FOR CARRYING OUT THE INVENTION

First Embodiment

Figure 1:
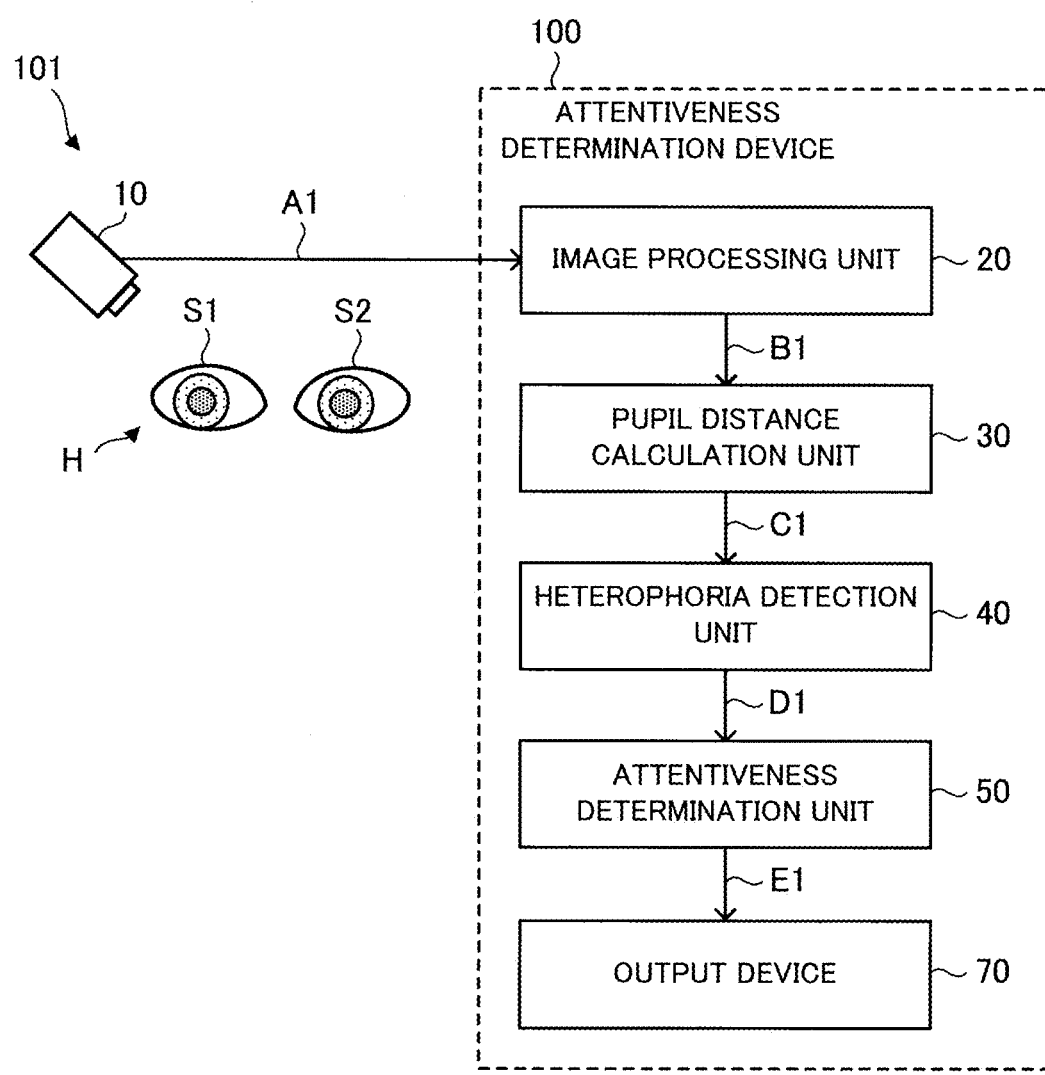
FIG. 1 is a block diagram schematically showing a configuration of an attentiveness determination system according to a first embodiment of the present invention.

FIG. 1 is a block diagram schematically showing a configuration of an attentiveness determination system 101 according to a first embodiment of the present invention.

The attentiveness determination system 101 includes an image capturing unit 10 and an attentiveness determination device 100 that uses an image captured by the image capturing unit 10 and including a first eyeball S1 and a second eyeball S2 of a person H.

The attentiveness determination device 100 includes an image processing unit 20, a pupil distance calculation unit 30, a heterophoria detection unit 40 and an attentiveness determination unit 50. The attentiveness determination device 100 determines the attentiveness of the person H by using the image including the first eyeball S1 and the second eyeball S2. The attentiveness determination device 100 may further include an output device 70.

The image captured by the image capturing unit 10 is an image including the face of the person H, for example. The image capturing unit 10 captures an image including at least the first eyeball S1 and the second eyeball S2 of the person H. In other words, the image including the face of the person H captured by the image capturing unit 10 is an image including at least the first eyeball S1 and the second eyeball S2 of the person H. In this embodiment, the first eyeball S1 is the right eye of the person H and the second eyeball S2 is the left eye of the person H. The image captured by the image capturing unit 10 may be either a still image or motion video.

Normally, the image capturing unit 10 captures an image including the first eyeball S1, the second eyeball S2 and a nose S3 of the person H. In this case, the image including the face of the person H captured by the image capturing unit 10 is an image including the first eyeball S1, the second eyeball S2 and the nose S3 of the person H.

The first eyeball S1 and the second eyeball S2 are objects that undergo a determination by the attentiveness determination unit 50.

The image captured by the image capturing unit 10 is referred to as a "captured image A1". The image capturing unit 10 outputs the captured image A1. In this embodiment, the image capturing unit 10 captures the image including the face of the person H periodically or continuously and outputs the captured image A1 periodically or continuously.

The image capturing unit 10 may include a memory that stores the captured images A1. In this case, the image capturing unit 10 is capable of storing the captured images A1 in the memory and outputting the captured images A1 stored in the memory.

The captured images A1 outputted from the image capturing unit 10 are inputted to the image processing unit 20.

Figure 2:
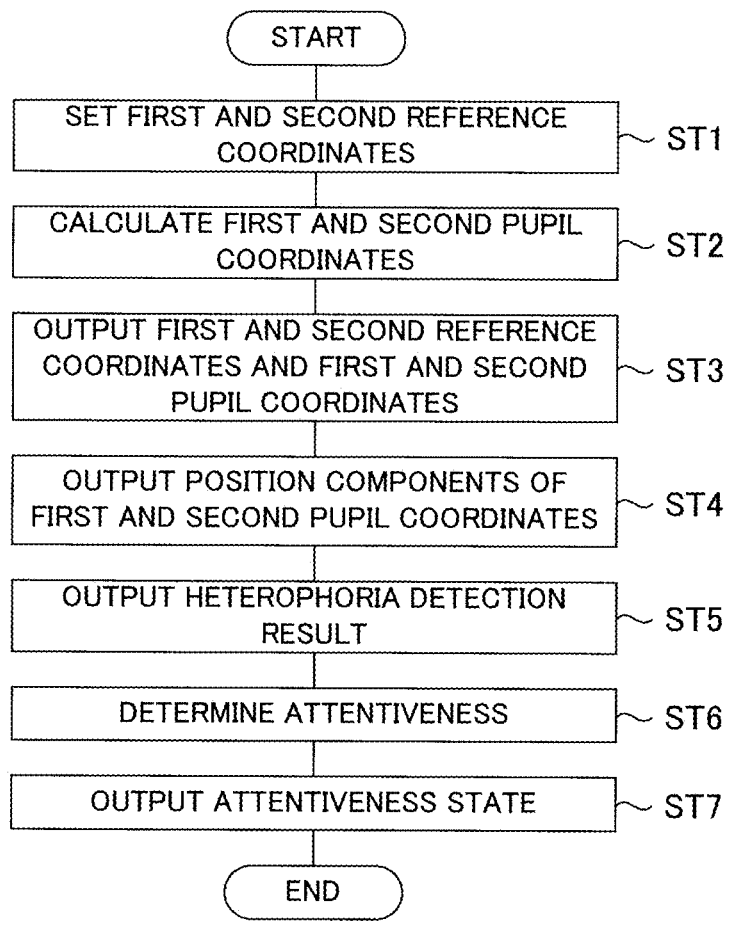
FIG. 2 is a flowchart showing an example of a process of an attentiveness determination method in the first embodiment.

FIG. 2 is a flowchart showing an example of a process in the aforementioned attentiveness determination system 101 regarding an attentiveness determination method for determining the attentiveness of the person H.

In step ST1, first reference coordinates regarding the first eyeball S1 and second reference coordinates regarding the second eyeball S2 are set in the captured image A1.

In step ST2, first pupil coordinates that are coordinates of a pupil 24 (referred to also as a first pupil of a right pupil) of the first eyeball S1 in the captured image A1 and second pupil coordinates that are coordinates of a pupil 25 (referred to also as a second pupil of a left pupil) of the second eyeball S2 in the captured image A1 are calculated.

In step ST3, the first reference coordinates, the second reference coordinates, the first pupil coordinates and the second pupil coordinates are outputted.

In step ST4, at least one position component of the first pupil coordinates with respect to the first reference coordinates and at least one position component of the second pupil coordinates with respect to the second reference coordinates are calculated.

In step ST5, a heterophoria detection result indicating a state of the first eyeball S1 and the second eyeball S2 is outputted by using the at least one position component of the first pupil coordinates and the at least one position component of the second pupil coordinates.

In step ST6, the attentiveness of the person H is determined according to the heterophoria detection result.

In step ST7, an attentiveness state E1 is outputted.

The above-described attentiveness determination method will be described concretely below.

The image processing unit 20 acquires the captured image A1. The image processing unit 20 generates output coordinates B1 by using the captured image A1 and outputs the generated output coordinates B1. The output coordinates B1 are data including at least one set of coordinates calculated by the image processing unit 20. The output coordinates B1 includes, for example, at least one set of reference coordinates, the first pupil coordinates Re (referred to also as right pupil coordinates) and the second pupil coordinates Le (referred to also as left pupil coordinates). The output coordinates B1 may further include other coordinates such as nose coordinates Nt.

Figure 3:
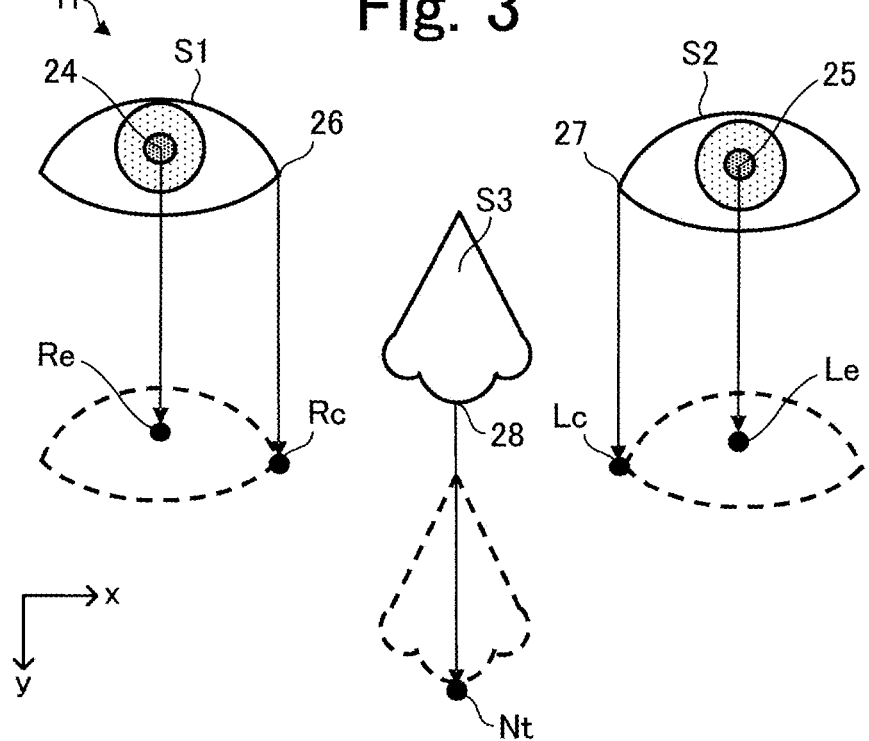
FIG. 3 is a diagram showing a correspondence relationship between positions of a first eyeball, a second eyeball and a nose of a person and positions of these elements in a captured image.

FIG. 3 is a diagram showing a correspondence relationship between positions of the first eyeball S1, the second eyeball S2 and the nose S3 of the person H and positions of these elements in the captured image A1.

In the orthogonal coordinate system shown in FIG. 3, an x-axis direction (x-axis) represents a lateral direction in the captured image A1, and a y-axis direction (y-axis) represents a direction orthogonal to the x-axis direction, that is, an up-down direction, in the captured image A1.

In the step ST1, the image processing unit 20 sets at least one set of reference coordinates in the captured image (i.e., the captured image A1). In this embodiment, the reference coordinates regarding the first eyeball S1 (referred to also as the first reference coordinates) and the reference coordinates regarding the second eyeball S2 (referred to also as the second reference coordinates) are set in the captured image A1.

In this embodiment, the image processing unit 20 selects coordinates of an eye inner corner 26 of the first eyeball S1 as the reference coordinates regarding the first eyeball S1, and sets the reference coordinates regarding the first eyeball S1 as first eye inner corner coordinates Rc. Similarly, the image processing unit 20 selects coordinates of an eye inner corner 27 of the second eyeball S2 as the reference coordinates regarding the second eyeball S2, and sets the reference coordinates regarding the second eyeball S2 as second eye inner corner coordinates Lc.

While the first eye inner corner coordinates Rc are used as the reference coordinates regarding the first eyeball S1 in this embodiment, it is also possible to use other coordinates as the reference coordinates regarding the first eyeball S1. Similarly, while the second eye inner corner coordinates Lc are used as the reference coordinates regarding the second eyeball S2, it is also possible to use other coordinates as the reference coordinates regarding the second eyeball S2. It is also possible to use the same coordinates as the reference coordinates regarding the first eyeball S1 and the second eyeball S2.

The first eye inner corner coordinates Rc are the coordinates of the eye inner corner 26 of the first eyeball S1 in the captured image A1, and the second eye inner corner coordinates Lc are the coordinates of the eye inner corner 27 of the second eyeball S2 in the captured image A1.

The first eye inner corner coordinates Rc are represented as coordinates (Rcx, Rcy), for example, and the second eye inner corner coordinates Lc are represented as coordinates (Lcx, Lcy), for example. Rcx represents the x coordinate of the eye inner corner 26, that is, the position of the eye inner corner 26 on the x-axis. Rcy represents the y coordinate of the eye inner corner 26, that is, the position of the eye inner corner 26 on the y-axis. Lcx represents the x coordinate of the eye inner corner 27, that is, the position of the eye inner corner 27 on the x-axis. Lcy represents the y coordinate of the eye inner corner 27, that is, the position of the eye inner corner 27 on the y-axis.

In the step ST2, the image processing unit 20 calculates the first pupil coordinates Re and the second pupil coordinates Le. The first pupil coordinates Re are the coordinates of the pupil 24 of the first eyeball S1 in the captured image A1. The second pupil coordinates Le are the coordinates of the pupil 25 of the second eyeball S2 in the captured image A1. The nose coordinates Nt are the coordinates of a nose tip end 28 of the nose S3 in the captured image A1. The nose tip end 28 is a tip end part of the nose S3 in the y-axis direction.

The first pupil coordinates Re are represented as coordinates (Rex, Rey), for example, the second pupil coordinates Le are represented as coordinates (Lex, Ley), for example, and the nose coordinates Nt are represented as coordinates (Ntx, Nty), for example. Rex represents the x coordinate of the pupil 24, that is, the position of the pupil 24 on the x-axis. Rey represents the y coordinate of the pupil 24, that is, the position of the pupil 24 on the y-axis. Lex represents the x coordinate of the pupil 25, that is, the position of the pupil 25 on the x-axis. Ley represents the y coordinate of the pupil 25, that is, the position of the pupil 25 on the y-axis. Ntx represents the x coordinate of the nose tip end 28, that is, the position of the nose tip end 28 on the x-axis. Nty represents the y coordinate of the nose tip end 28, that is, the position of the nose tip end 28 on the y-axis.

In the step ST3, the image processing unit 20 outputs at least one set of pupil coordinates and at least one set of reference coordinates as the output coordinates B1. In this embodiment, the image processing unit 20 outputs the first pupil coordinates Re, the second pupil coordinates Le, the first reference coordinates and the second reference coordinates.

For example, when the image processing unit 20 sets the first eye inner corner coordinates Rc as the first reference coordinates and the second eye inner corner coordinates Lc as the second reference coordinates, the image processing unit 20 outputs the first pupil coordinates Re, the second pupil coordinates Le, the first eye inner corner coordinates Rc and the second eye inner corner coordinates Lc as the output coordinates B1. In this case, the output coordinates B1 are represented as a one-dimensional sequence (i.e., B1=[Rex, Rey, Lex, Ley, Rcx, Rcy, Lcx, Lcy]), for example.

Figure 4:
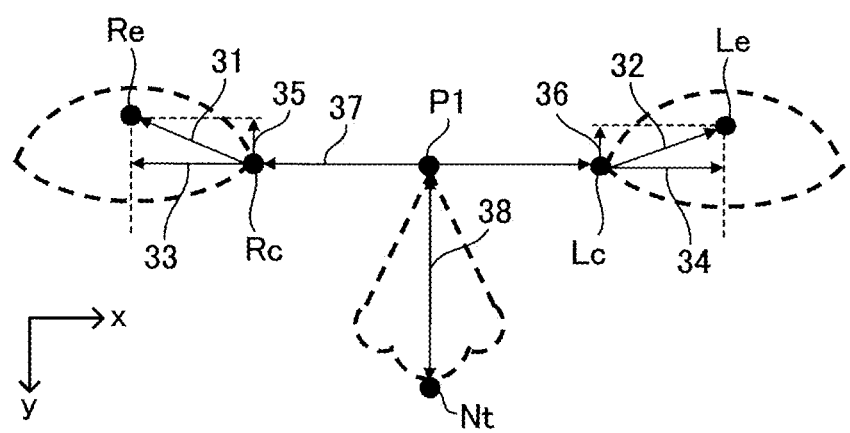
FIG. 4 is a diagram showing a method of calculating a pupil distance.

FIG. 4 is a diagram showing a method of calculating the pupil distance.

The output coordinates B1 are inputted to the pupil distance calculation unit 30. By using the output coordinates B1, the pupil distance calculation unit 30 calculates a pupil distance 31 (referred to also as a first pupil distance), a pupil distance 32 (referred to also as a second pupil distance), a pupil distance 33 (referred to also as a third pupil distance), a pupil distance 34 (referred to also as a fourth pupil distance), a pupil distance 35 (referred to also as a fifth pupil distance) and a pupil distance 36 (referred to also as a sixth pupil distance).

The pupil distance calculation unit 30 calculates the pupil distances 31, 32, 33, 34, 35 and 36 periodically. By the calculation, time-series data is obtained by the pupil distance calculation unit 30.

Specifically, the pupil distance calculation unit 30 periodically calculates at least one position component of the first pupil coordinates Re with respect to the first reference coordinates in the captured image A1 and at least one position component of the second pupil coordinates Le with respect to the second reference coordinates in the captured image A1. In this embodiment, position components of the first pupil coordinates Re are the pupil distances 31, 33 and 35, and position components of the second pupil coordinates Le are the pupil distances 32, 34 and 36.

The pupil distance 31 is the distance from a first reference position to the pupil 24. In the captured image A1, the pupil distance 31 is the distance from the first eye inner corner coordinates Rc as the first reference coordinates to the first pupil coordinates Re. In this embodiment, the distance from the first eye inner corner coordinates Rc to the first pupil coordinates Re in the captured image A1 is assumed to be R.

The pupil distance 32 is the distance from a second reference position to the pupil 25. In the captured image A1, the pupil distance 32 is the distance from the second eye inner corner coordinates Lc as the second reference coordinates to the second pupil coordinates Le. In this embodiment, the distance from the second eye inner corner coordinates Lc to the second pupil coordinates Le in the captured image A1 is assumed to be L.

The pupil distance 33 is the distance from the first reference position to the pupil 24 in the lateral direction. In the captured image A1, the pupil distance 33 is the distance from the first eye inner corner coordinates Rc as the first reference coordinates to the first pupil coordinates Re in the lateral direction in the captured image A1. In this embodiment, the distance from the first eye inner corner coordinates Rc to the first pupil coordinates Re in the lateral direction in the captured image A1 is assumed to be Rh.

The pupil distance 34 is the distance from the second reference position to the pupil 25 in the lateral direction. In the captured image A1, the pupil distance 34 is the distance from the second eye inner corner coordinates Lc as the second reference coordinates to the second pupil coordinates Le in the lateral direction in the captured image A1. In this embodiment, the distance from the second eye inner corner coordinates Lc to the second pupil coordinates Le in the lateral direction in the captured image A1 is assumed to be Lh.

The pupil distance 35 is the distance from the first reference position to the pupil 24 in the up-down direction. In the captured image A1, the pupil distance 35 is the distance from the first eye inner corner coordinates Rc as the first reference coordinates to the first pupil coordinates Re in the up-down direction in the captured image A1. In this embodiment, the distance from the first eye inner corner coordinates Rc to the first pupil coordinates Re in the up-down direction in the captured image A1 is assumed to be Rv.

The pupil distance 36 is the distance from the second reference position to the pupil 25 in the up-down direction. In the captured image A1, the pupil distance 36 is the distance from the second eye inner corner coordinates Lc as the second reference coordinates to the second pupil coordinates Le in the up-down direction in the captured image A1. In this embodiment, the distance from the second eye inner corner coordinates Lc to the second pupil coordinates Le in the up-down direction in the captured image A1 is assumed to be Lv.

When the image processing unit 20 selects the first eye inner corner coordinates Rc and the second eye inner corner coordinates Lc respectively as the first reference coordinates and the second reference coordinates, the distance Rh is represented as |Rcx−Rex|, the distance Lh is represented as |Lcx−Lex|, the distance Rv is represented as |Rcy−Rey|, and the distance Lv is represented as |Lcy−Ley|.

In this case, the distance R is represented by expression (1) by using the distance Rh and the distance Rv, and the distance L is represented by expression (2) by using the distance Lh and the distance Lv.

$$R=\sqrt{Rh^2+Rv^2} \qquad (1)$$

$$L=\sqrt{Lh^2+Lv^2} \qquad (2)$$

In the step ST4, the pupil distance calculation unit 30 outputs the calculated distances Rh, Lh, Rv, Lv, R and L as pupil distance output C1. The pupil distance output C1 is represented as a one-dimensional sequence (i.e., C1=[Rh, Lh, Rv, Lv, R, L]), for example.

The pupil distance output C1 is inputted to the heterophoria detection unit 40. The heterophoria detection unit 40 calculates fluctuation in the position of the pupil 24 and fluctuation in the position of the pupil 25 in a predetermined period by using at least one position component of the first pupil coordinates Re and at least one position component of the second pupil coordinates Le. Further, the heterophoria detection unit 40 determines eyeball movement of the person H by using a result of calculating the fluctuation in the position of the pupil 24 and the fluctuation in the position of the pupil 25.

In other words, the heterophoria detection unit 40 determines the eyeball movement of the person H by using fluctuation in components of the pupil distance output C1 as time-series data. The components of the pupil distance output C1 are the distances Rh, Lh, Rv, Lv, R and L.

Specifically, by using the fluctuation in components of the pupil distance output C1, the heterophoria detection unit 40 determines whether the state of both eyes of the person H is both eyes movement (referred to also as a both eyes movement state) or monocular eyeball movement (e.g., a heterophoric state) of the person H. For example, when both of the fluctuation in the position of the pupil 24 and the fluctuation in the position of the pupil 25 are greater than or equal to a threshold value or less than or equal to a threshold value, the heterophoria detection unit 40 determines that the state of both eyes of the person H is the both eyes movement state. In contrast, when one of the fluctuation in the position of the pupil 24 or the fluctuation in the position of the pupil 25 is greater than or equal to a threshold value and the other is less than a threshold value, the heterophoria detection unit 40 determines that one of the first eyeball S1 or the second eyeball S2 is in the heterophoric state (i.e., ocular deviation). The heterophoria detection unit 40 may use either one threshold value or two or more threshold values.

The fluctuation in a component of the pupil distance output C1 is represented as variance, for example.

Since the heterophoria detection unit 40 makes the determination between the both eyes movement state and the heterophoric state, the attentiveness of the person H can be determined according to the result of the determination between the both eyes movement state and the heterophoric state.

FIG. 5A to FIG. 5D are diagrams showing examples of the both eyes movement (i.e., the both eyes movement state) of the person H.

Figure 5A:
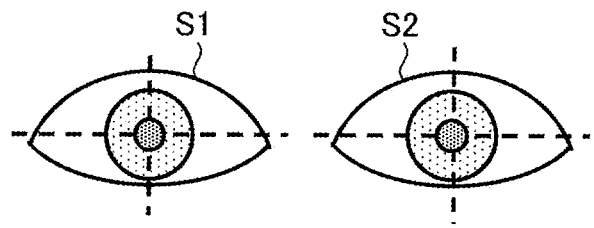
FIGS. 5A to 5D are diagrams showing examples of both eyes movement of a person.

FIG. 5A shows an ocular fixation state. The ocular fixation state is a state in which the left and right eyeballs are fixed and a state in which the person H is fixing his/her eyes on a visual target.

Figure 5B:
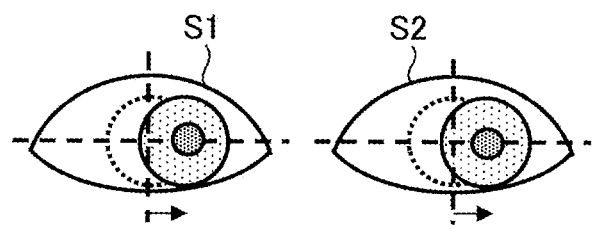

FIG. 5B is a diagram showing a line-of-sight movement state in the lateral direction.

For example, when the distance Rh increases and the distance Lh decreases, it is determined that the line of sight of the person H is pointed to the right. In contrast, when the distance Rh decreases and the distance Lh increases, it is determined that the line of sight of the person H is pointed to the left.

Figure 5C:
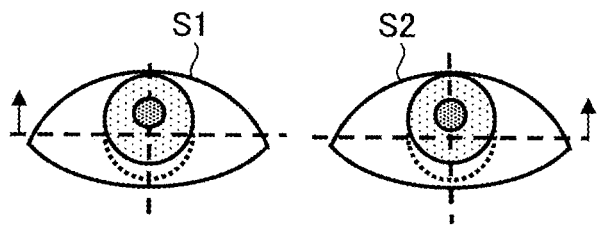

FIG. 5C is a diagram showing a line-of-sight movement state in the up-down direction.

For example, when the distance Rv and the distance Lv increase, it is determined that the line of sight of the person His pointed upward. In contrast, when the distance Rv and the distance Lv decrease, it is determined that the line of sight of the person His pointed downward. When the distance R and the distance L increase, it is determined that the line of sight of the person H is pointed in an oblique direction.

Figure 5D:
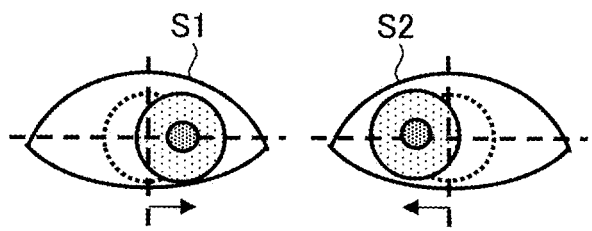

FIG. 5D is a diagram showing a convergence movement state. The convergence movement is a movement of directing both eyes towards the nose. That is, the convergence movement state is a state in which both eyes of the person H are performing the convergence movement. For example, when the distance Rh and the distance Lh decrease, the state of both eyes of the person H is determined to be the convergence movement state.

The both eyes movement of the person H is not limited to the examples shown in FIG. 5A to FIG. 5D. For example, when the distance Rh and the distance Lh increase, it is determined that both eyes of the person H are performing a divergence movement. The divergence movement is a movement of directing both eyes towards the ears.

FIG. 6A to FIG. 6D are diagrams showing examples of the monocular eyeball movement, specifically, the heterophoric state, of the person H.

In general, as ocular positions of the human, there are a binocular vision position, a fusion-free position, a physiological rest position and an absolute rest position. In the binocular vision position, extraocular muscles and intraocular muscles are strained to implement the binocular vision function. In the fusion-free position, fusional convergence for the fusion of images inputted to the left and right eyeballs is removed. The physiological rest position appears in a deep sleep, for example, in which stimuli received by the ocular muscles decrease to the minimum. The absolute rest position appears after death, for example, in which the ocular muscles are released from all types of stimuli.

The heterophoria means potentially having the fusion-free position although usually having the binocular vision function by straining ocular muscles, that is, a state of temporarily approaching the fusion-free position when the strain of the ocular muscles becomes insufficient. When the fusional convergence is gradually lost from the state in which the binocular vision function works, ocular deviation appears in one eye as the heterophoria, in which the direction of the line of sight varies from person to person.

For example, when a variance value σr that is the variance value of the distance R is less than a threshold value Tr and a variance value σl that is the variance value of the distance L is greater than or equal to Tl, the heterophoria detection unit 40 can determine that the person H is (i.e., the first eyeball S1 and the second eyeball S2 are) in one of the heterophoric states shown in FIG. 6A to FIG. 6D.

Figure 6A:
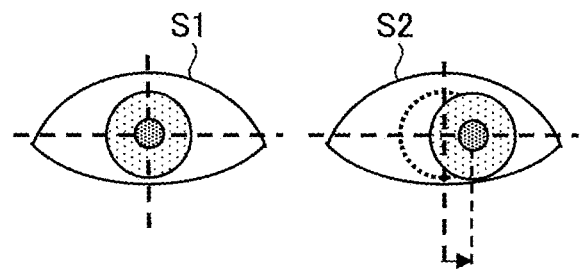
FIGS. 6A to 6D are diagrams showing examples of monocular eyeball movement, specifically, a heterophoric state, of the person.

FIG. 6A shows an exophoric state. The exophoric state is a state in which one of the pupil of the first eyeball S1 or the pupil of the second eyeball S2 is directed towards the ear's side. For example, when the distance Rh is constant and the distance Lh increases as shown in FIG. 6A, the first eyeball S1 and the second eyeball S2 are determined to be in the exophoric state. Similarly, when the distance Rh increases and the distance Lh is constant, the first eyeball S1 and the second eyeball S2 are determined to be in the exophoric state.

Figure 6B:
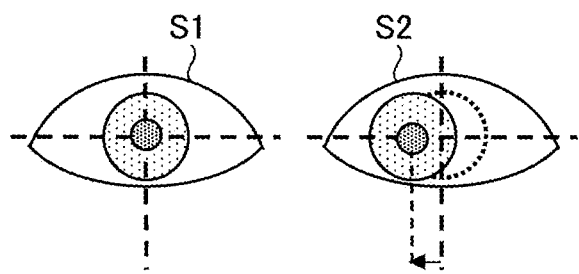

FIG. 6B shows an esophoric state. The esophoric state is a state in which one of the pupil of the first eyeball S1 or the pupil of the second eyeball S2 is directed towards the nose's side. For example, when the distance Rh is constant and the distance Lh decreases as shown in FIG. 6B, the first eyeball S1 and the second eyeball S2 are determined to be in the esophoric state. Similarly, when the distance Rh decreases and the distance Lh is constant, the first eyeball S1 and the second eyeball S2 are determined to be in the esophoric state.

Figure 6C:
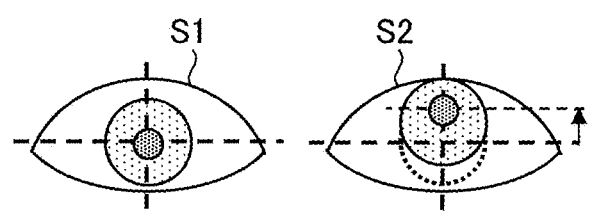

FIG. 6C shows an anaphoric state. The anaphoric state is a state in which one of the pupil of the first eyeball S1 or the pupil of the second eyeball S2 is directed upward. For example, when the distance Rv is constant and the distance Lv increases as shown in FIG. 6C, the first eyeball S1 and the second eyeball S2 are determined to be in the anaphoric state. Similarly, when the distance Rv increases and the distance Lv is constant, the first eyeball S1 and the second eyeball S2 are determined to be in the anaphoric state.

Figure 6D:
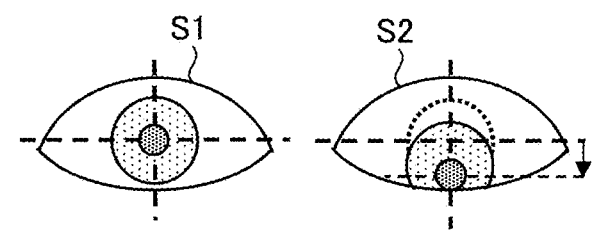

FIG. 6D shows a hypophoric state. The hypophoric state is a state in which one of the pupil of the first eyeball S1 or the pupil of the second eyeball S2 is directed downward. For example, when the distance Rv is constant and the distance Lv decreases as shown in FIG. 6D, the first eyeball S1 and the second eyeball S2 are determined to be in the hypophoric state. Similarly, when the distance Rv decreases and the distance Lv is constant, the first eyeball S1 and the second eyeball S2 are determined to be in the hypophoric state.

The heterophoric state is not limited to the examples shown in FIG. 6A to FIG. 6D. For example, when one of the exophoric state or the esophoric state and one of the anaphoric state or the hypophoric state occur at the same time, the first eyeball S1 and the second eyeball S2 are determined to be heterophoric in an oblique direction.

When the heterophoria detection unit 40 determines the state of both eyes of the person H, the heterophoria detection unit 40 calculates variance values σrh, σlh, σrv, σlv, σr and σl of the components included in the pupil distance output C1 by using time-series data, for example. In this case, the time-series data is the pupil distance output C1 periodically inputted to the heterophoria detection unit 40.

The variance value σrh is the variance value of the distance Rh inputted to the heterophoria detection unit 40 in a predetermined period. The variance value σlh is the variance value of the distance Lh inputted to the heterophoria detection unit 40 in the predetermined period. The variance value σrv is the variance value of the distance Rv inputted to the heterophoria detection unit 40 in the predetermined period. The variance value σlv is the variance value of the distance Lv inputted to the heterophoria detection unit 40 in the predetermined period. The variance value σr is the variance value of the distance R inputted to the heterophoria detection unit 40 in the predetermined period. The variance value σl is the variance value of the distance L inputted to the heterophoria detection unit 40 in the predetermined period.

The heterophoria detection unit 40 compares the variance value of each component with a predetermined threshold value (referred to also as a "fluctuation threshold value") corresponding to the variance value.

The threshold value corresponding to the variance value σrh is a threshold value Trh. The threshold value corresponding to the variance value σlh is a threshold value Tlh. The threshold value corresponding to the variance value σrv is a threshold value Trv. The threshold value corresponding to the variance value σlv is a threshold value Tlv. The threshold value corresponding to the variance value σr is a threshold value Tr. The threshold value corresponding to the variance value σl is a threshold value Tl.

Each of the threshold values Trh, Tlh, Trv, Tlv, Tr and Tl is a predetermined value. As each threshold value, it is possible to use the variance value of each component included in the pupil distance output C1 in a predetermined period, or a value obtained by weighting a variance value acquired from time-series data in the ocular fixation state with a weight.

For example, the heterophoria detection unit 40 determines whether or not data regarding the first eyeball S1 satisfies a first condition (i.e., σrh<Trh, σrv<Trv and σr<Tr) and determines whether or not data regarding the second eyeball S2 satisfies a second condition (i.e., σlh<Tlh, σlv<Tlv and σl<Tl).

When the first condition (i.e., σrh<Trh, σrv<Trv and σr<Tr) is satisfied, the heterophoria detection unit 40 determines that the first eyeball S1 of the person H is in the ocular fixation state.

In contrast, when the first condition is not satisfied, the heterophoria detection unit 40 determines that the first eyeball S1 of the person H is not in the ocular fixation state. That is, the heterophoria detection unit 40 determines that the first eyeball S1 is moving in some direction.

When the second condition (i.e., σlh<Tlh, σlv<Tlv and σl<Tl) is satisfied, the heterophoria detection unit 40 determines that the second eyeball S2 of the person H is in the ocular fixation state.

In contrast, when the second condition is not satisfied, the heterophoria detection unit 40 determines that the second eyeball S2 of the person H is not in the ocular fixation state. That is, the heterophoria detection unit 40 determines that the second eyeball S2 is moving in some direction.

When the data regarding the first eyeball S1 and the second eyeball S2 do not satisfy both of the first condition and the second condition, the heterophoria detection unit 40 determines that the first eyeball S1 and the second eyeball S2 are performing both eyes movement such as sight line movement in the up-down direction, sight line movement in the lateral direction, convergence movement or divergence movement. In other words, when the data regarding the first eyeball S1 and the second eyeball S2 do not satisfy both of the first condition and the second condition, the heterophoria detection unit 40 determines that the state of the first eyeball S1 and the second eyeball S2 is the both eyes movement state.

When the data regarding the first eyeball S1 and the second eyeball S2 satisfy only one of the first condition or the second condition, the heterophoria detection unit 40 determines that the ocular deviation of one eye of the person H occurs. In this case, the heterophoria detection unit 40 determines that the state of the person H is the heterophoric state. In other words, the heterophoria detection unit 40 determines that one of the first eyeball S1 or the second eyeball S2 is in the heterophoric state.

By determining behavior of both eyes of the person H, it is possible to determine whether the first eyeball S1 and the second eyeball S2 are in the both eyes movement state or one of the first eyeball S1 or the second eyeball S2 is in the heterophoric state.

The heterophoria detection unit 40 has only to determine whether the first eyeball S1 and the second eyeball S2 are in the both eyes movement state or one of the first eyeball S1 or the second eyeball S2 is in the heterophoric state. The above-described determination method of the heterophoria detection unit 40 is just an example and various determination conditions may be combined together.

In the step ST5, the heterophoria detection unit 40 outputs the result of the determination as a heterophoria detection result D1. The heterophoria detection result D1 indicates the state of the first eyeball S1 and the second eyeball S2. For example, the heterophoria detection result D1 indicates whether the first eyeball S1 and the second eyeball S2 are in the both eyes movement state or one of the first eyeball S1 or the second eyeball S2 is in the heterophoric state.

The heterophoria detection result D1 is inputted to the attentiveness determination unit 50. In the step ST6, the attentiveness determination unit 50 determines the attentiveness of the person H according to the heterophoria detection result D1 and generates the result of the determination as the attentiveness state E1.

The attentiveness state E1 is, for example, an attentiveness deteriorating state or an attentiveness maintaining state. In this case, the attentiveness deteriorating state is a state in which the attentiveness of the person H is low, and the attentiveness maintaining state is a state in which the attentiveness of the person H is high.

For example, when the heterophoria detection result D1 indicates the both eyes movement state, the attentiveness determination unit 50 determines that the person H is in the attentiveness maintaining state and generates the attentiveness state E1 as a signal indicating the attentiveness maintaining state. In contrast, when the heterophoria detection result D1 indicates the heterophoric state, the attentiveness determination unit 50 determines that the person H is in the attentiveness deteriorating state and generates the attentiveness state E1 as a signal indicating the attentiveness deteriorating state.

In the step ST7, the attentiveness determination unit 50 outputs the attentiveness state E1. The attentiveness state E1 is inputted to the output device 70 such as a monitor, a head-up display, a speaker or a vibrator, for example. Depending on the attentiveness state E1, the output device 70 outputs at least one of an image (e.g., a still image or motion video), audio, or vibration, for example. When the attentiveness state E1 is not the attentiveness deteriorating state, the output device 70 does not need to output anything.

Figure 7A:
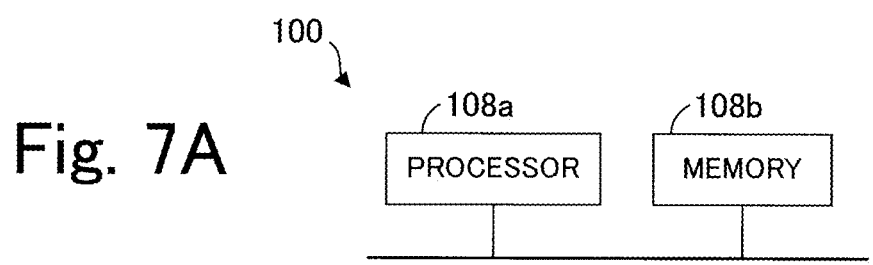
FIG. 7A is a diagram showing an example of a hardware configuration of an attentiveness determination device.

FIG. 7A is a diagram showing an example of a hardware configuration of the attentiveness determination device 100.

Figure 7B:
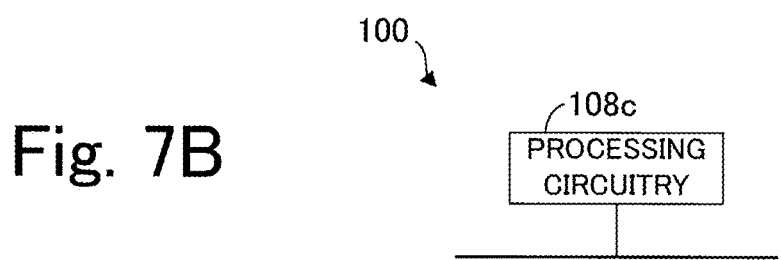
FIG. 7B is a diagram showing another example of the hardware configuration of the attentiveness determination device.

FIG. 7B is a diagram showing another example of the hardware configuration of the attentiveness determination device 100.

The attentiveness determination device 100 is formed of at least one processor 108a and at least one memory 108b, for example. The processor 108a is, for example, a central processing unit (CPU) that executes a program stored in the memory 108b. In this case, the functions of the attentiveness determination device 100 are implemented by software, firmware, or a combination of software and firmware. The software and the firmware can be stored in the memory 108b as programs. With this configuration, a program for implementing the functions of the attentiveness determination device 100 (e.g., the attentiveness determination method described in this embodiment) is executed by a computer.

The memory 108b as a computer-readable storage medium is, for example, a volatile memory, a nonvolatile memory, or a combination of a volatile memory and a nonvolatile memory such as a RAM (Random Access Memory) and a ROM (Read Only Memory).

The attentiveness determination device 100 may also be formed of processing circuitry 108c as dedicated hardware such as a single circuit or a combined circuit. In this case, the functions of the attentiveness determination device 100 are implemented by the processing circuitry 108c.

As described above, the attentiveness determination device 100 in this first embodiment detects whether or not the ocular deviation occurs in the person H. Therefore, the attentiveness determination device 100 is capable of determining the attentiveness by using images captured at a low frame rate. Accordingly, the attentiveness determination device 100 does not need high processing power of the CPU in comparison with the device that detects the saccade that is a high-speed eye movement. As a result, the production cost of the attentiveness determination device 100 can be reduced.

The attentiveness determination system 101 according to the first embodiment includes the attentiveness determination device 100. Accordingly, the attentiveness determination system 101 has advantages the same as the aforementioned advantages of the attentiveness determination device 100.

Second Embodiment

Figure 8:
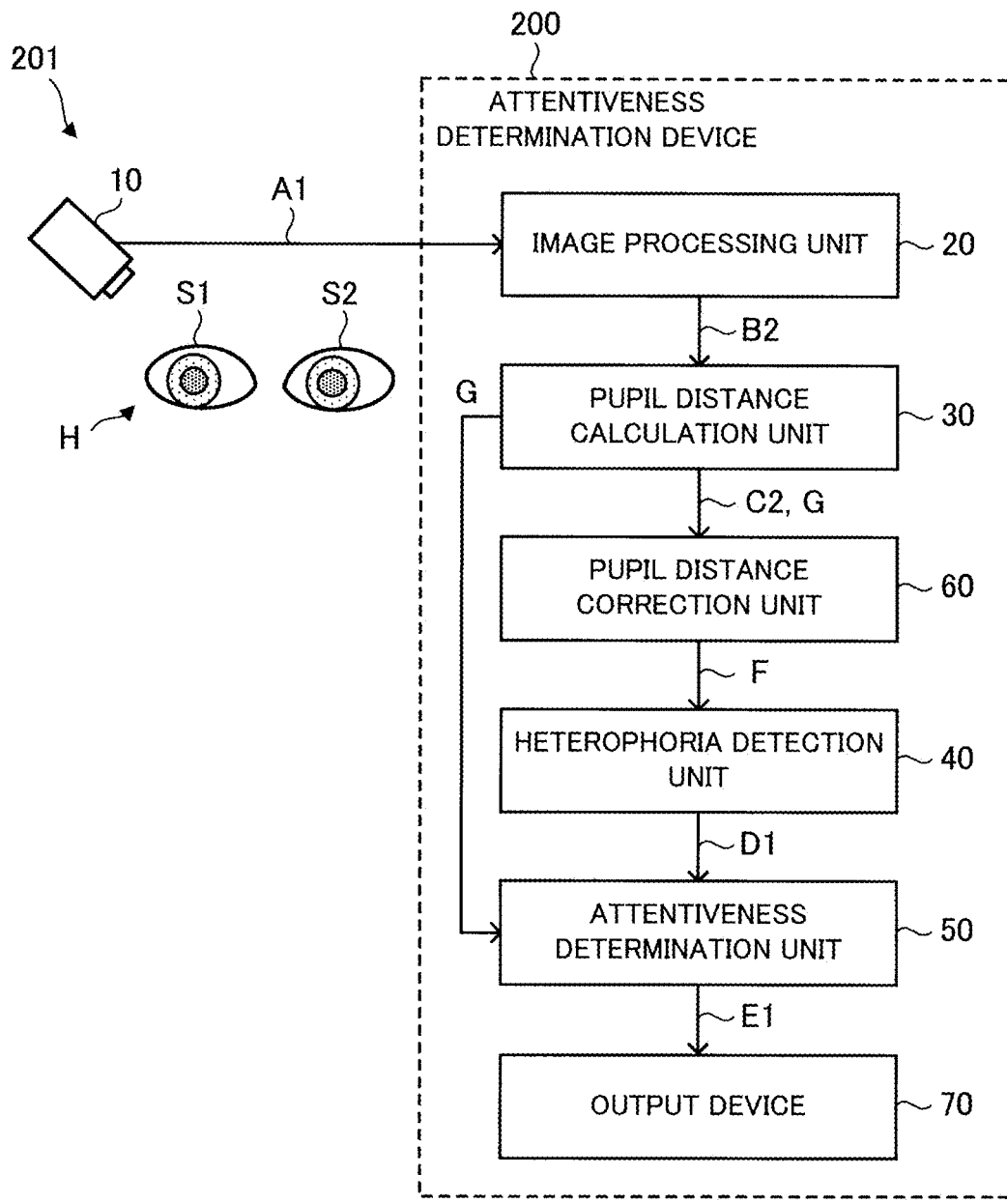
FIG. 8 is a block diagram schematically showing a configuration of an attentiveness determination system according to a second embodiment of the present invention.

FIG. 8 is a block diagram schematically showing a configuration of an attentiveness determination system 201 according to a second embodiment of the present invention.

Figure 9:
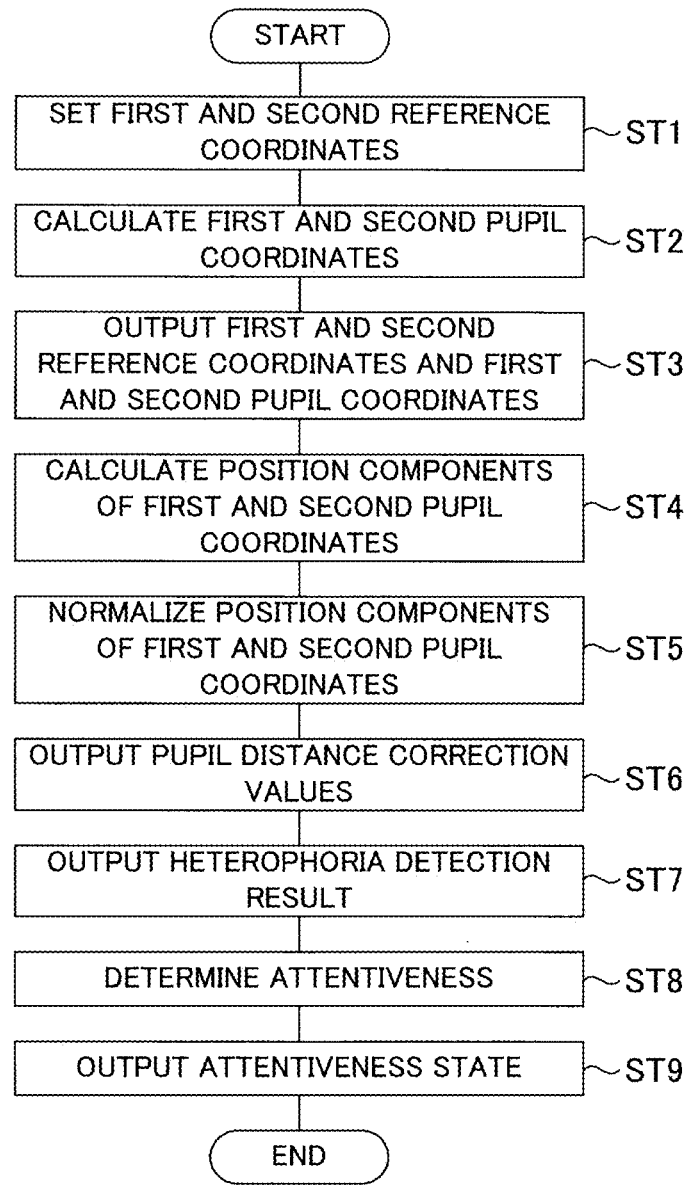
FIG. 9 is a flowchart showing an example of a process of an attentiveness determination method in the second embodiment.

FIG. 9 is a flowchart showing an example of a process in the aforementioned attentiveness determination system 201 regarding an attentiveness determination method for determining the attentiveness of a person H.

In step ST1, the first reference coordinates regarding the first eyeball S1 and the second reference coordinates regarding the second eyeball S2 are set in the captured image A1.

In step ST2, the first pupil coordinates that are the coordinates of the pupil of the first eyeball S1 in the captured image A1 and the second pupil coordinates that are the coordinates of the pupil of the second eyeball S2 in the captured image A1 are calculated.

In step ST3, the first reference coordinates, the second reference coordinates, the first pupil coordinates and the second pupil coordinates are outputted.

In step ST4, at least one position component of the first pupil coordinates with respect to the first reference coordinates and at least one position component of the second pupil coordinates with respect to the second reference coordinates are calculated.

In step ST5, the at least one position component of the first pupil coordinates and the at least one position component of the second pupil coordinates are normalized.

In step ST6, the normalized values are outputted as pupil distance correction values.

In step ST7, the heterophoria detection result indicating the state of the first eyeball S1 and the second eyeball S2 is outputted by using the pupil distance correction values.

In step ST8, the attentiveness of the person H is determined according to the heterophoria detection result.

In step ST9, the attentiveness state E1 is outputted.

In the second embodiment, the description will be given mainly of configurations and operations different from those in the first embodiment.

The attentiveness determination system 201 according to the second embodiment includes an attentiveness determination device 200 instead of the attentiveness determination device 100. In the second embodiment, the attentiveness determination device 200 uses images including the first eyeball S1, the second eyeball S2 and the nose S3 of the person H captured by the image capturing unit 10.

The attentiveness determination device 200 includes the image capturing unit 10, the image processing unit 20, the pupil distance calculation unit 30, the heterophoria detection unit 40, the attentiveness determination unit 50 and a pupil distance correction unit 60. Put another way, the attentiveness determination device 200 according to the second embodiment includes the pupil distance correction unit 60 in addition to the image capturing unit 10, the image processing unit 20, the pupil distance calculation unit 30, the heterophoria detection unit 40 and the attentiveness determination unit 50 described in the first embodiment. The attentiveness determination device 200 may further include the output device 70.

The attentiveness determination device 200 determines the attentiveness of the person H by using the images including the first eyeball S1, the second eyeball S2 and the nose S3.

The hardware configuration of the attentiveness determination device 200 may be the same as the hardware configuration described in the first embodiment. In this case, the hardware configuration of the attentiveness determination device 200 is the hardware configuration shown in FIG. 7A or FIG. 7B.

In the step ST2, the image processing unit 20 further calculates the first eye inner corner coordinates Rc of the first eyeball S1, the second eye inner corner coordinates Lc of the second eyeball S2 and the nose coordinates Nt in addition to the first pupil coordinates Re and the second pupil coordinates Le.

In the step ST3, the image processing unit 20 outputs at least one set of pupil coordinates, the nose coordinates Nt and at least one set of reference coordinates as output coordinates B2. In this embodiment, the image processing unit 20 outputs the first pupil coordinates Re, the second pupil coordinates Le, the nose coordinates Nt, the first reference coordinates and the second reference coordinates as the output coordinates B2.

For example, when the image processing unit 20 sets the first eye inner corner coordinates Rc as the first reference coordinates and the second eye inner corner coordinates Lc as the second reference coordinates similarly to the second embodiment, the image processing unit 20 outputs the first pupil coordinates Re, the second pupil coordinates Le, the nose coordinates Nt, the first eye inner corner coordinates Rc and the second eye inner corner coordinates Lc as the output coordinates B2. In this case, the output coordinates B2 are represented as a one-dimensional sequence (i.e., B2=[Rex, Rey, Lex, Ley, Rcx, Rcy, Lcx, Lcy, Ntx, Nty]), for example.

The output coordinates B2 are inputted to the pupil distance calculation unit 30. In the step ST4, by using the output coordinates B2, the pupil distance calculation unit 30 periodically calculates an eye inner corner distance 37 and a nose bridge distance 38 in addition to the pupil distances 31, 32, 33, 34, 35 and 36. By the calculation, time-series data is obtained by the pupil distance calculation unit 30.

The eye inner corner distance 37 is the distance between the first eyeball S1 and the second eyeball S2. Specifically, the eye inner corner distance 37 is the distance between the eye inner corner 26 of the first eyeball S1 and the eye inner corner 27 of the second eyeball S2. In the captured image A1, the eye inner corner distance 37 is the distance from the first eye inner corner coordinates Rc to the second eye inner corner coordinates Lc. In this embodiment, the distance from the first eye inner corner coordinates Rc to the second eye inner corner coordinates Lc in the captured image A1 is assumed to be D.

The nose bridge distance 38 is the distance between a midpoint P1 of the eye inner corner distance 37 and the nose tip end 28. In the captured image A1, the nose bridge distance 38 is the distance from the midpoint P1 to the nose coordinates Nt. In this embodiment, the distance from the midpoint P1 to the nose coordinates Nt in the captured image A1 is assumed to be N.

The distance D is represented by the following expression (3):

$$D=\sqrt{(Lcx-Rcx)^2+(Lcy+Rcy)^2} \qquad (3)$$

The distance N is represented by the following expression (4):

$$N=\sqrt{((Lcx+Rcx)/2-Ntx)^2+((Lcy+Rcy)/2-Nty)^2} \qquad (4)$$

The pupil distance calculation unit 30 outputs the calculated distances Rh, Lh, Rv, Lv, R, L, D and N as pupil distance output C2. The pupil distance output C2 is represented as a one-dimensional sequence (i.e., C2=[Rh, Lh, Rv, Lv, R, L, D, N]), for example.

Further, the pupil distance calculation unit 30 may output the calculated distances D and N as reference value output G. The reference value output G is represented as a one-dimensional sequence (i.e., G=[D, N]), for example.

The pupil distance output C2 and the reference value output G are inputted to the pupil distance correction unit 60. In the step ST5, the pupil distance correction unit 60 normalizes the pupil distance, that is, at least one position component of the first pupil coordinates Re and at least one position component of the second pupil coordinates Le, by using at least one arbitrary value.

In this embodiment, the pupil distance correction unit 60 normalizes the pupil distance, that is, at least one position component of the first pupil coordinates Re and at least one position component of the second pupil coordinates Le, by using the eye inner corner distance 37 (i.e., the distance D) or the nose bridge distance 38 (i.e., the distance N).

Specifically, the pupil distance correction unit 60 normalizes the pupil distance 33 and the pupil distance 34 by using the eye inner corner distance 37. For example, the pupil distance 33 is normalized by Rh/D, and the pupil distance 34 is normalized by Lh/D.

The pupil distance correction unit 60 normalizes the pupil distance 35 and the pupil distance 36 by using the nose bridge distance 38. For example, the pupil distance 35 is normalized by Rv/N, and the pupil distance 36 is normalized by Lv/N.

The pupil distance correction unit 60 updates the pupil distance 31 by using the normalized pupil distance 35. For example, the updated pupil distance 31 is represented by the following expression (5):

$$R=\sqrt{(Rh/D)^2+(Rv/N)^2} \quad (5)$$

The pupil distance correction unit 60 updates the pupil distance 32 by using the normalized pupil distance 36. For example, the updated pupil distance 32 is represented by the following expression (6):

$$L=\sqrt{(Lh/D)^2+(Lv/N)^2} \quad (6)$$

In the step ST6, the pupil distance correction unit 60 outputs the normalized values (i.e., normalized position components) as pupil distance correction values F. The pupil distance correction values F are represented as a one-dimensional sequence (i.e., F=[Rh/D, Lh/D, Rv/N, Lv/N, R, L]), for example.

The pupil distance correction values F are inputted to the heterophoria detection unit 40. In the step ST7, the heterophoria detection unit 40 outputs the heterophoria detection result indicating the state of the first eyeball S1 and the second eyeball S2 by using the pupil distance correction values F. Specifically, the heterophoria detection unit 40 determines the eyeball movement of the person H, that is, the state of both eyes of the person H, by using fluctuation in the pupil distance correction values F. More specifically, the heterophoria detection unit 40 determines whether the state of both eyes of the person H is the both eyes movement or the monocular eyeball movement of the person H by using the fluctuation in the pupil distance correction values F. The heterophoria detection unit 40 outputs the result of the determination as the heterophoria detection result.

When the heterophoria detection unit 40 determines the state of both eyes of the person H, the heterophoria detection unit 40 calculates variance values of the components included in the pupil distance correction values F by using time-series data, for example. In this case, the time-series data is the pupil distance correction values F periodically inputted to the heterophoria detection unit 40.

The heterophoria detection unit 40 compares the variance value of each component with a predetermined threshold value (referred to also as a "fluctuation threshold value") corresponding to the variance value.

As described in the first embodiment, the heterophoria detection unit 40 determines whether or not data regarding the first eyeball S1 satisfies the first condition, determines whether or not data regarding the second eyeball S2 satisfies the second condition, and outputs the result of the determination as the heterophoria detection result D1.

The heterophoria detection result D1 is inputted to the attentiveness determination unit 50. Further, the reference value output G, that is, time-series data of the eye inner corner distance 37 and the nose bridge distance 38, is inputted to the attentiveness determination unit 50. In the example shown in FIG. 8, the reference value output G is inputted from the pupil distance calculation unit 30 to the attentiveness determination unit 50. However, the reference value output G may also be inputted from a component other than the pupil distance calculation unit 30 (e.g., the heterophoria detection unit 40 or the pupil distance correction unit 60) to the attentiveness determination unit 50.

In the step ST8, the attentiveness determination unit 50 calculates a variance value σd of the eye inner corner distance 37 by using the time-series data of the eye inner corner distance 37 and calculates a variance value σn by using the time-series data of the nose bridge distance 38. The attentiveness determination unit 50 compares the calculated variance values with a fluctuation threshold value.

Specifically, the attentiveness determination unit 50 compares the calculated variance value σd with a fluctuation threshold value Td and compares the calculated variance value σn with a fluctuation threshold value Tn.

The fluctuation threshold value Td is a predetermined value. For example, as the fluctuation threshold value Td, it is possible to use the variance value of the eye inner corner distance 37 in a predetermined period, or a value obtained by weighting a variance value acquired from time-series data in the ocular fixation state with a weight. Similarly, the fluctuation threshold value Tn is a predetermined value. For example, as the fluctuation threshold value Tn, it is possible to use the variance value of the nose bridge distance 38 in a predetermined period, or a value obtained by weighting a variance value acquired from time-series data in the ocular fixation state with a weight.

When the time-series data (specifically, the variance value σd regarding the eye inner corner distance 37 and the variance value σn regarding the nose bridge distance 38) satisfies an attentiveness condition (i.e., σd<Td and σn<Tn), the change in the face direction of the person H is small. Thus, when the time-series data satisfies the attentiveness condition (i.e., σd<Td and σn<Tn), the attentiveness determination unit 50 determines that the person H is in the attentiveness deteriorating state and generates the attentiveness state E1 indicating the attentiveness deteriorating state.

In contrast, when the variance value σd is greater than or equal to the fluctuation threshold value Td, the face direction of the person H is moving widely in the Pitch direction (y-axis direction in FIG. 3). When the variance value σn is greater than or equal to the fluctuation threshold value Tn, the face direction of the person H is moving widely in the Yaw direction (x-axis direction in FIG. 3).

That is, when the time-series data (specifically, the variance value σd regarding the eye inner corner distance 37 and the variance value σn regarding the nose bridge distance 38) does not satisfy the attentiveness condition (i.e., σd<Td and σn<Tn), the face direction of the person H is moving widely in the Pitch direction and the Yaw direction. In this case, the attentiveness determination unit 50 determines that the person H is sufficiently viewing the surroundings. Therefore, when the time-series data does not satisfy the attentiveness condition, the attentiveness determination unit 50 determines that the person H is in the attentiveness maintaining state and generates the attentiveness state E1 indicating the attentiveness maintaining state.

In the step ST9, the attentiveness determination unit 50 outputs the attentiveness state E1.

The attentiveness determination device 200 in the second embodiment has advantages the same as the advantages of the attentiveness determination device 100 in the first embodiment.

Further, the attentiveness determination device 200 according to the second embodiment determines the attentiveness of the person H by using the eye inner corner distance 37 and the nose bridge distance 38. The eye inner corner distance 37 and the nose bridge distance 38 can be regarded as fixed indices of the person H. Therefore, by normalizing the pupil distances (e.g., the pupil distances 33, 34, 35 and 36) by using the eye inner corner distance 37 or the nose bridge distance 38, influence of fluctuation in the pupil distances due to a minute change in the face direction of the person H can be reduced. As a result, accuracy of the analysis of the time-series data of the pupil distances (e.g., the pupil distances 33, 34, 35 and 36) can be increased.

The attentiveness determination system 201 including the attentiveness determination device 200 has advantages the same as the aforementioned advantages of the attentiveness determination device 200.

Features in the embodiments described above can be appropriately combined with each other.

DESCRIPTION OF REFERENCE CHARACTERS

10: image capturing unit, 20: image processing unit, 30: pupil distance calculation unit, 40: heterophoria detection unit, 50: attentiveness determination unit, 60: pupil distance correction unit, 70: output device, 100, 200: attentiveness determination device, 101, 201: attentiveness determination system.

What is claimed is:

1. An attentiveness determination device to use a captured image including a first eyeball and a second eyeball of a person, comprising:
    a processor to execute a program; and
    a memory to store the program which, when executed by the processor, performs processes of,
    setting first reference coordinates regarding the first eyeball and second reference coordinates regarding the second eyeball in the captured image, calculating first pupil coordinates that are coordinates of a pupil of the first eyeball in the captured image and second pupil coordinates that are coordinates of a pupil of the second eyeball in the captured image, and outputting the first reference coordinates, the second reference coordinates, the first pupil coordinates, and the second pupil coordinates;
    calculating at least one position component of the first pupil coordinates with respect to the first reference coordinates and at least one position component of the second pupil coordinates with respect to the second reference coordinates;
    outputting a heterophoria detection result indicating a state of the first eyeball and the second eyeball by using the at least one position component of the first pupil coordinates and the at least one position component of the second pupil coordinates; and
    determining attentiveness of the person according to the heterophoria detection result.

2. The attentiveness determination device according to claim 1, wherein
    the at least one position component of the first pupil coordinates includes a distance from the first reference coordinates to the first pupil coordinates, and
    the at least one position component of the second pupil coordinates includes a distance from the second reference coordinates to the second pupil coordinates.

3. The attentiveness determination device according to claim 1, wherein the program, when executed by the processor, further performs processes of
    calculating fluctuation in a position of the pupil of the first eyeball and fluctuation in a position of the pupil of the second eyeball by using the at least one position component of the first pupil coordinates and the at least one position component of the second pupil coordinates, and
    determining the state of the first eyeball and the second eyeball by using a result of calculating the fluctuation in the position of the pupil of the first eyeball and the fluctuation in the position of the pupil of the second eyeball.

4. The attentiveness determination device according to claim 1, wherein the program, when executed by the processor, further performs processes of
    determining that the first eyeball and the second eyeball are in both eyes movement when both of fluctuation in a position of the pupil of the first eyeball and fluctuation in a position of the pupil of the second eyeball are greater than or equal to a threshold value or less than or equal to the threshold value, and
    determining that one of the first eyeball or the second eyeball is in a heterophoric state when one of fluctuation in a position of the pupil of the first eyeball or fluctuation in a position of the pupil of the second eyeball is greater than or equal to the threshold value and the other is less than the threshold value.

5. The attentiveness determination device according to claim 1, wherein the heterophoria detection result indicates whether the first eyeball and the second eyeball are in a both eyes movement state or one of the first eyeball or the second eyeball is in a heterophoric state.

6. The attentiveness determination device according to claim 5, wherein the program, when executed by the processor, further performs processes of
    determining that the person is in an attentiveness maintaining state when the heterophoria detection result indicates the both eyes movement state, and
    determining that the person is in an attentiveness deteriorating state when the heterophoria detection result indicates the heterophoric state.

7. The attentiveness determination device according to claim 6, wherein the program, when executed by the processor, further performs processes of
    outputting a signal indicating the attentiveness deteriorating state or the attentiveness maintaining state of the person according to the heterophoria detection result.

8. An attentiveness determination system comprising:
    the attentiveness determination device according to claim 1; and
    an image capturing unit to capture the captured image including the first eyeball and the second eyeball of the person.

9. An attentiveness determination device to use a captured image including a first eyeball and a second eyeball of a person, comprising:
    a processor to execute a program; and
    a memory to store the program which, when executed by the processor, performs processes of,
    setting first reference coordinates regarding the first eyeball and second reference coordinates regarding the second eyeball in the captured image, calculating first pupil coordinates that are coordinates of a pupil of the first eyeball in the captured image and second pupil coordinates that are coordinates of a pupil of the second eyeball in the captured image, and outputting the first reference coordinates, the second reference coordinates, the first pupil coordinates, and the second pupil coordinates;

calculating at least one position component of the first pupil coordinates with respect to the first reference coordinates and at least one position component of the second pupil coordinates with respect to the second reference coordinates;

normalizing the at least one position component of the first pupil coordinates and the at least one position component of the second pupil coordinates and outputting the normalized values as pupil distance correction values;

outputting a heterophoria detection result indicating a state of the first eyeball and the second eyeball by using the pupil distance correction values; and determining attentiveness of the person according to the heterophoria detection result.

10. An attentiveness determination system comprising:
the attentiveness determination device according to claim 8; and
an image capturing unit to capture the captured image including the first eyeball and the second eyeball of the person.

11. An attentiveness determination method of determining attentiveness of a person by using a captured image including a first eyeball and a second eyeball of the person, the attentiveness determination method comprising:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates, and the second pupil coordinates;

calculating at least one position component of the first pupil coordinates with respect to the first reference coordinates and at least one position component of the second pupil coordinates with respect to the second reference coordinates;

outputting a heterophoria detection result indicating a state of the first eyeball and the second eyeball by using the at least one position component of the first pupil coordinates and the at least one position component of the second pupil coordinates; and determining the attentiveness of the person according to the heterophoria detection result.

12. An attentiveness determination method of determining attentiveness of a person by using a captured image including a first eyeball and a second eyeball of the person, the attentiveness determination method comprising:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates, and the second pupil coordinates;

calculating at least one position component of the first pupil coordinates with respect to the first reference coordinates and at least one position component of the second pupil coordinates with respect to the second reference coordinates;

normalizing the at least one position component of the first pupil coordinates and the at least one position component of the second pupil coordinates;

outputting the normalized values as pupil distance correction values;

outputting a heterophoria detection result indicating a state of the first eyeball and the second eyeball by using the pupil distance correction values; and determining the attentiveness of the person according to the heterophoria detection result.

13. A non-transitory computer-readable storage medium storing a program that causes a computer to execute an attentiveness determination method of determining attentiveness of a person by using a captured image including a first eyeball and a second eyeball of the person, the program causing the computer to execute:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates, and the second pupil coordinates;

calculating at least one position component of the first pupil coordinates with respect to the first reference coordinates and at least one position component of the second pupil coordinates with respect to the second reference coordinates;

outputting a heterophoria detection result indicating a state of the first eyeball and the second eyeball by using the at least one position component of the first pupil coordinates and the at least one position component of the second pupil coordinates; and determining the attentiveness of the person according to the heterophoria detection result.

14. A non-transitory computer-readable storage medium storing a program that causes a computer to execute an attentiveness determination method of determining attentiveness of a person by using a captured image including a first eyeball and a second eyeball of the person, the program causing the computer to execute:

setting first reference coordinates regarding the first eyeball and second reference coordinates regarding the second eyeball in the captured image;

calculating first pupil coordinates that are coordinates of a pupil of the first eyeball in the captured image and second pupil coordinates that are coordinates of a pupil of the second eyeball in the captured image;

outputting the first reference coordinates, the second reference coordinates, the first pupil coordinates, and the second pupil coordinates;

calculating at least one position component of the first pupil coordinates with respect to the first reference coordinates and at least one position component of the second pupil coordinates with respect to the second reference coordinates;

normalizing the at least one position component of the first pupil coordinates and the at least one position component of the second pupil coordinates;

outputting the normalized values as pupil distance correction values;

outputting a heterophoria detection result indicating a state of the first eyeball and the second eyeball by using the pupil distance correction values; and determining the attentiveness of the person according to the heterophoria detection result.

* * * * *